(12) United States Patent
Watson et al.

(10) Patent No.: US 7,737,405 B2
(45) Date of Patent: Jun. 15, 2010

(54) TIME-OF-FLIGHT (TOF) POSITRON EMISSION TOMOGRAPHY (PET) RECONSTRUCTION FROM TIME-TRUNCATED PROJECTION DATA

(75) Inventors: Charles C. Watson, Knoxville, TN (US); Vladimir Panin, Knoxville, TN (US); Bernard Bendriem, Knoxville, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/212,130

(22) Filed: Sep. 17, 2008

(65) Prior Publication Data

US 2009/0072155 A1 Mar. 19, 2009

Related U.S. Application Data

(60) Provisional application No. 60/972,894, filed on Sep. 17, 2007.

(51) Int. Cl.
*G01T 1/164* (2006.01)

(52) U.S. Cl. .................................... 250/363.03
(58) Field of Classification Search ............. 250/363.03
See application file for complete search history.

(56) References Cited

U.S. PATENT DOCUMENTS

2004/0234450 A1* 11/2004 Howes .................. 424/1.11

OTHER PUBLICATIONS

Defrise, Michael et al., "Fourier rebinning of time-of-flight PET data", Physics in Medicine and Biology, No. 50, pp. 2749-2763, May 25, 2005.*

* cited by examiner

*Primary Examiner*—David P Porta
*Assistant Examiner*—Mark R Gaworecki
(74) *Attorney, Agent, or Firm*—Peter L. Kendall

(57) ABSTRACT

A method of TOF-PET image reconstruction using time-truncated TOF-PET projection data. The time-truncated TOF-PET data is obtained by narrowing the scanner time window to a smaller "time window field of view," which reduces the field of view of a TOF-PET scanner. This results in a lower list mode stream transfer rate, which can be useful in high count rate data acquisitions, in particular $^{82}$Rb cardiac studies.

12 Claims, 4 Drawing Sheets

TIME-OF-FLIGHT (TOF) POSITRON EMISSION TOMOGRAPHY (PET) RECONSTRUCTION FROM TIME-TRUNCATED PROJECTION DATA

CROSS-REFERENCE TO RELATED APPLICATION AND CLAIM OF PRIORITY

This application claims benefit under 35 U.S.C. §119(e) to copending provisional application Ser. No. 60/972,894 filed Sep. 17, 2007, which is incorporated herein by reference in its entirety.

FIELD OF THE INVENTION

The present invention relates generally to nuclear medicine and systems for obtaining nuclear medicine images. In particular, the present invention relates to reconstructing nuclear medicine images from time-of-flight (TOF) positron emission tomography (PET) data that has been time-truncated.

BACKGROUND OF THE INVENTION

Nuclear medicine is a unique specialty wherein radiation is used to acquire images which show the function and anatomy of organs, bones or tissues of the body. The technique of acquiring nuclear medicine images entails first introducing radiopharmaceuticals into the body—either by injection or ingestion. These radiopharmaceuticals are attracted to specific organs, bones or tissues of interest (These exemplary organs, bones, or tissues are also more generally referred to herein using the term "objects".). Upon arriving at their specified area of interest, the radiopharmaceuticals produce gamma photon emissions which emanate from the body and are then captured by a scintillation crystal. The interaction of the gamma photons with the scintillation crystal produces flashes of light which are referred to as "events." Events are detected by an array of photo detectors (such as photomultiplier tubes) and their spatial locations or positions are then calculated and stored. In this way, an image of the organ or tissue under study is created from detection of the distribution of the radioisotopes in the body.

One particular nuclear medicine imaging technique is known as positron emission tomography, or PET. PET is used to produce images for diagnosing the biochemistry or physiology of a specific organ, tumor or other metabolically active site. The measurement of tissue concentration using a positron emitting radionuclide is based on coincidence detection of the two gamma photons arising from a positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors; i.e., the gamma photon emissions are detected virtually simultaneously by each detector. When two oppositely disposed gamma photons each strike an oppositely disposed detector to produce a time coincidence event, they also identify a line(s)-of-response (LOR) along which the annihilation event has occurred. An example of a PET method and apparatus is described in U.S. Pat. No. 6,858,847, which patent is incorporated herein by reference in its entirety.

After being sorted into parallel projections, the LOR defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LOR, where each set is parallel to a particular detector angle, and therefore represents a two dimensional parallel projection p(s, φ) of the three dimensional radionuclide distribution within the patient—where "s" corresponds to the distance of the LOR from the center of the detector and "φ" corresponds to the angle of the detector plane with respect to the x axis in (x, y) coordinate space (in other words, φ corresponds to a particular LOR direction).

Coincidence events are integrated or collected for each LOR and stored in a sinogram. In this format, a single fixed point in f(x, y) traces a sinusoid in the sinogram. In each sinogram, there is one row containing the LOR for a particular azimuthal angle φ; each such row corresponds to a one-dimensional parallel projection of the tracer distribution at a different coordinate along the scanner axis. This is shown conceptually in FIG. 1.

An event is registered if both crystals detect an annihilation photon within a coincidence time window τ (e.g., on the order of 4-5 nsec), depending on the timing properties of the scintillator and the field of view (FOV). The FOV is defined as the volume between the detectors; and a pair of detectors is sensitive only to coincidence events occurring in the FOV. Therefore, the need for physical collimation is eliminated and sensitivity is significantly increased. Accurate corrections (for example, attenuation correction) can be made for the self-absorption of photons within the patient so that accurate measurements of tracer concentration can be made.

The number of time coincidences detected per second within a FOV of a detector is the count rate of the detector. The count rate at each of two oppositely disposed detectors, A and B, can be referred to as singles counts or $S_A$ and $S_B$, respectively. The time required for a gamma photon to travel from its point of origin to a point of detection is referred to as the time-of-flight (TOF) of the gamma photon. TOF is dependent upon the speed of light c and the distance traveled. A time coincidence or coincidence event is identified if the time difference between the arrivals of signals in a pair of oppositely disposed detectors is within the coincidence time window τ. In conventional PET, the coincidence detection time window τ is wide enough so that an annihilation event occurring anywhere within the object will produce annihilation gamma photons reaching their respective detectors within the coincidence window. Coincidence time windows of 4.5-12 nsec are common for conventional PET, and are largely determined by the time resolution capabilities of the detectors and electronics.

As illustrated in FIG. 2, if an annihilation event occurs at the midpoint of a LOR, the TOF of the gamma photon detected in detector A ($T_A$) is equal to the TOF of the gamma photon detected in detector B ($T_B$) If an annihilation event occurs at a distance Δx from the midpoint of the LOR, the difference between $T_A$ and $T_B$ is Δt =2Δx/c, where c is the speed of light. If d is the distance between detectors, the TOF difference Δt could take any value from −d/c to +d/c, depending on the location of the annihilation event.

Time-of-flight (TOF) positron emission tomography (PET) ("TOF-PET") is based on the measurement of the difference Δt between the detection times of the two gamma photons arising from the positron annihilation event. This measurement allows the annihilation event to be localized along the LOR with a resolution of about 75-120 mm FWHM, assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects. Thus, in TOF-PET, the "TOF" coordinate, $\Delta t$, is stored together with s and $\phi$.

Local tomography refers to the ability to reconstruct an image from truncated or incomplete projection data. Such cases typically arise when the object to be imaged is relatively large, the entire object is not sufficiently measured, and the projection data are truncated due to a small detector size and resulting small field of view (FOV). Here, the truncated projection data is in the radial direction as the small FOV cannot directly detect gamma photons from outside the FOV. In this case, because the distribution of activity extends beyond a region of interest (ROI) that is targeted by the FOV, some of this activity from outside the FOV is received by the detector and represents artifact data. However, in such cases, a small ROI can be sufficiently measured, and the small ROI is able to be exactly reconstructed.

Because TOF-PET data includes $\Delta t$ information in addition to LOR information, the present inventors have investigated the possibility of truncating data acquisition in the time direction as opposed to the radial direction which would be useful in significantly high count rate acquisitions, such as $^{82}$Rb PET imaging scans.

SUMMARY OF THE INVENTION

The present invention provides a method of TOF-PET image reconstruction using time-truncated TOF-PET projection data. Such time-truncated TOF-PET data is obtained by narrowing the scanner time window to a smaller "time window field of view." This results in a lower list mode stream transfer rate, which can be useful in high count rate data acquisitions.

DETAILED DESCRIPTION OF THE INVENTION

Figure 1:
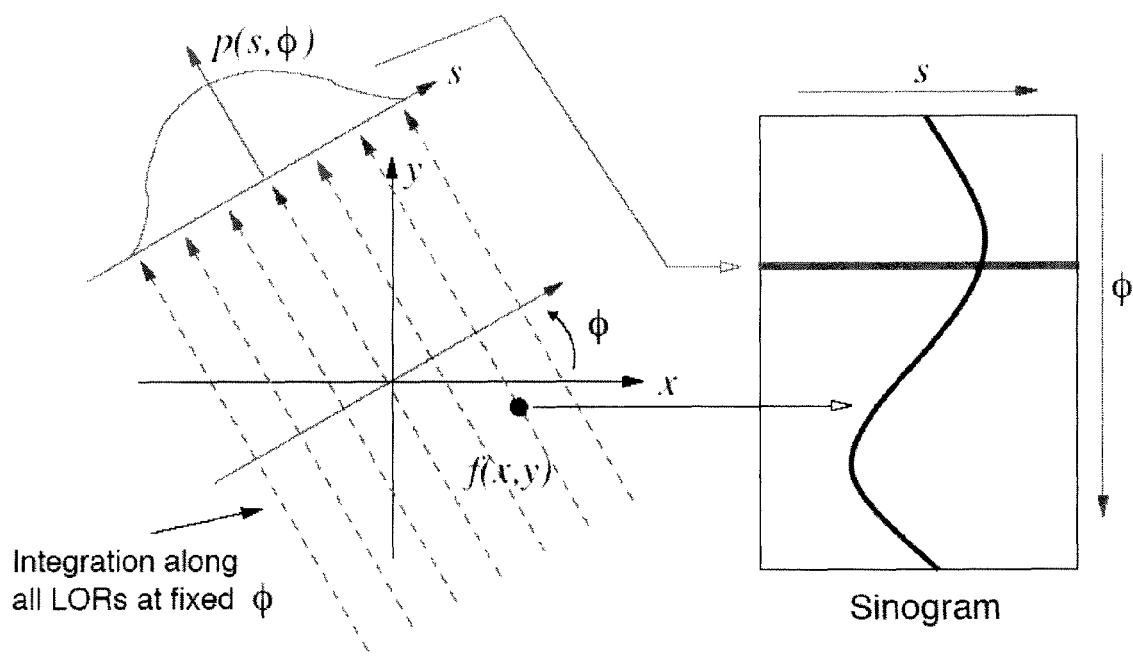
FIG. 1 is a prior art diagram illustrating an example of the relationship between positron emission data and a sinogram.
Figure 2:
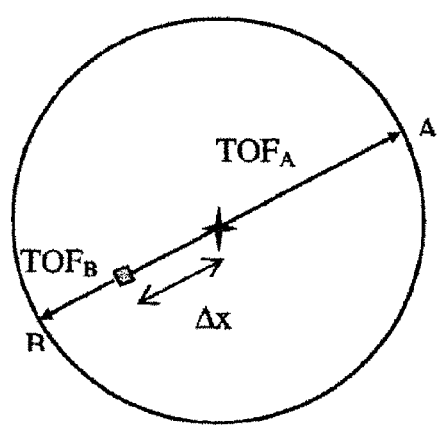
FIG. 2 is a prior art diagram illustrating the concept of time-of-flight (TOE) in positron emission tomography (PET) imaging.

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

The present invention provides a method of image reconstruction from TOF-PET projection data that has been truncated in the time direction. Such time truncation is unique to TOF-PET data because only TOF-PET includes a time parameter. The truncation of acquired TOF-PET projection data is obtained by time window narrowing. This results in a lower transfer rate of a list mode data stream, which can be useful in high count rate data acquisitions, such as $^{82}$Rb cardiac studies. An advantage of time data truncation as related to radial data truncation is that radial tails information is preserved, thus providing reliable source information for scaling in scatter correction estimation calculations.

It is not apparent from consideration of image reconstruction of radially truncated projection data that local tomography reconstruction of TOF-PET data truncated in the time direction would be possible. However, one variation of a 2D TOF FBP (Filtered Back-Projection) reconstruction algorithm proves this local tomography property. TOF projections are defined as:

$$p(\phi, r, t) = \int d\vec{x} f(\vec{x}) \delta(\vec{x} \cdot \vec{u}_\perp - r) g_\sigma(t - \vec{x} \cdot \vec{u})$$

where $\vec{u}_\perp = (\cos \phi, \sin \phi)$: $\vec{u} = (-\sin \phi, \cos \phi)$. $\phi$ is the azimuthal angle, r is the radial coordinate, and t is the time coordinate. The TOF profile is Gaussian:

$$g_\sigma(t) = \frac{\exp\left(-\frac{t^2}{2\sigma^2}\right)}{\sqrt{2\pi}\,\sigma}$$

The FBP formula (wherein projections are convolved in both the time and radial directions) states:

$$f(\vec{x}) = \int_0^\pi d\phi \{\{\mathrm{ramp}(r) g_\sigma(r)\} \otimes p(\phi, r, t)\} \Big|_{t=\vec{x}\cdot\vec{u}}^{r=\vec{x}\cdot\vec{u}_\perp}$$

From this, it can be seen that local tomography with respect to t is possible, in that image reconstruction of a specific local region requires only the TOF bins that contribute to that specific local region. For example, uniform truncation of TOF data will result in exact reconstruction of a central circular region. The local tomography property is also extended to 3D reconstruction, as there is exact TOF rebinning applied for each t separately.

Thus, in an iterative reconstruction algorithm such as OS-EM, one can expect that a local tomography region will be reconstructed exactly. Further, while the extent of reconstruction outside of the local tomography region at the moment is not totally clear, it can be expected that an image outside of the time window FOV can be reconstructed to some degree.

Figure 3:
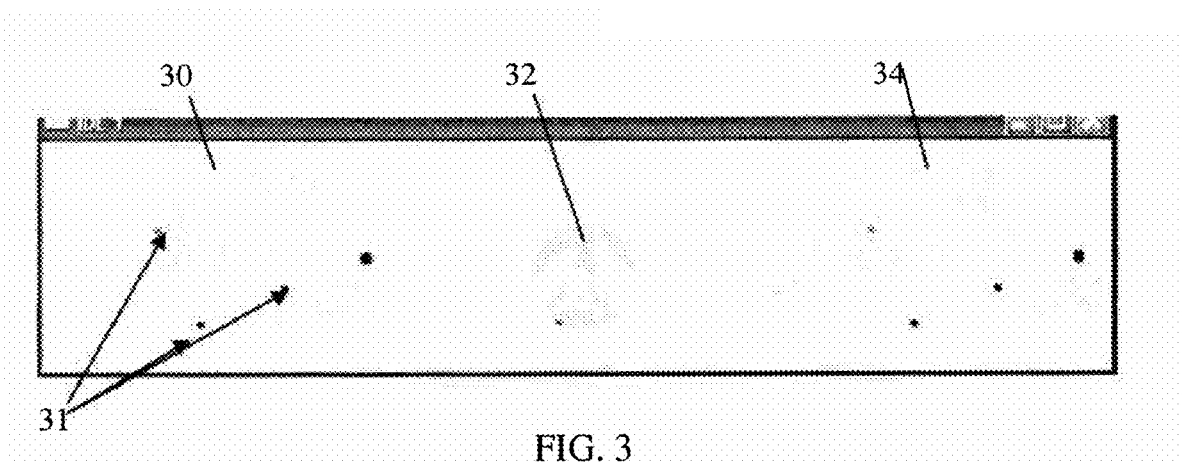
FIG. 3 shows a relationship between an original image, a truncated time window FOV, and a image reconstruction from the time-truncated data, in accordance with the present invention.
Figure 4A:
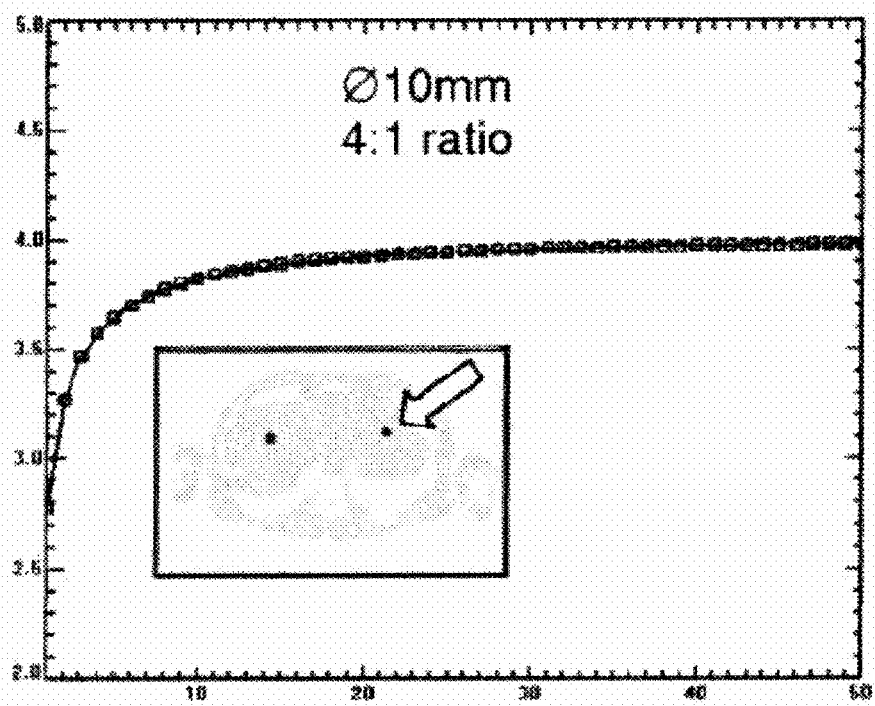
FIGS. 4A-4E illustrate the recovery of "hot" spheres in time-truncated TOF-PET as a function of iteration number, in accordance with the invention.
Figure 4B:
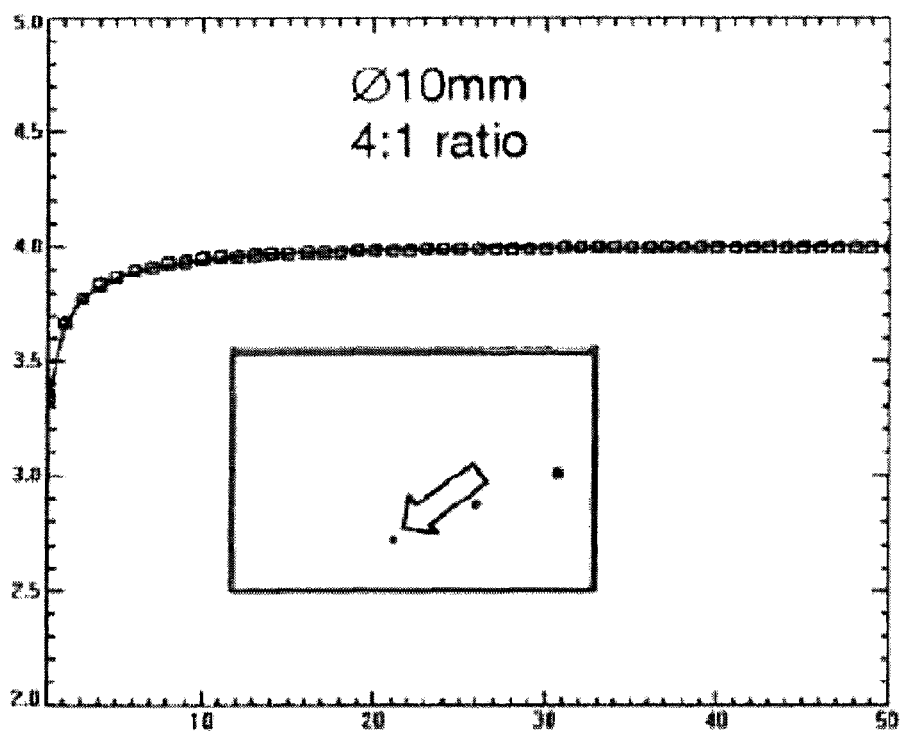
Figure 4C:
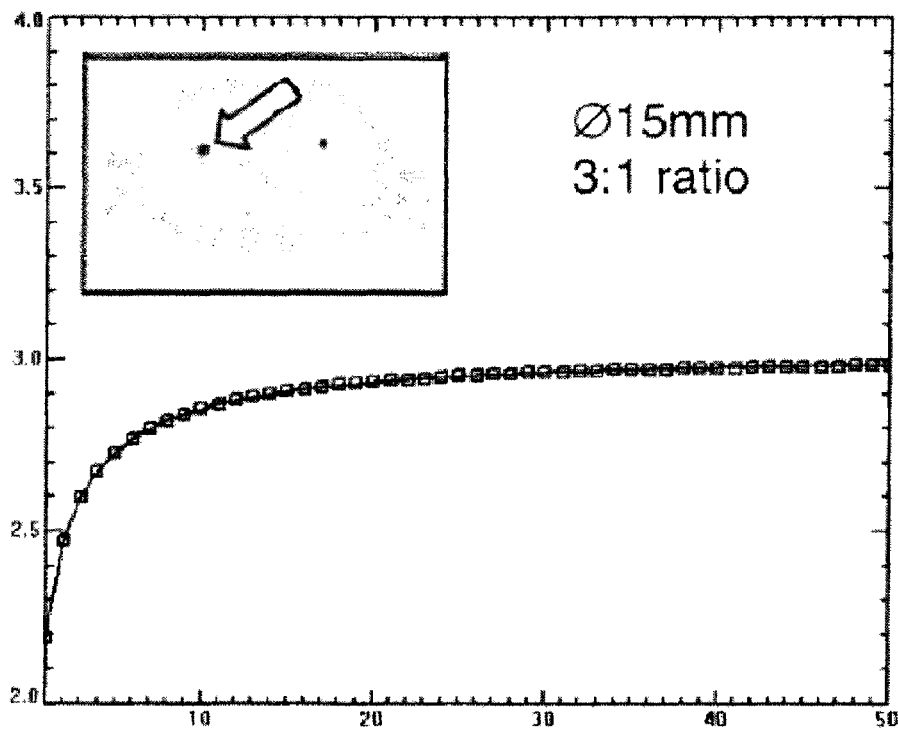
Figure 4D:
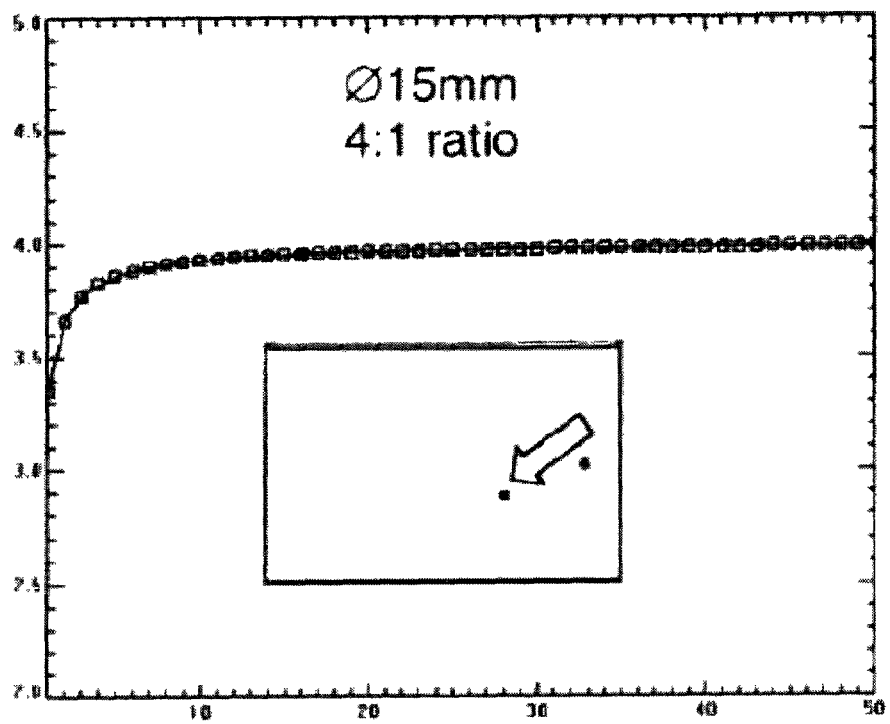
Figure 4E:
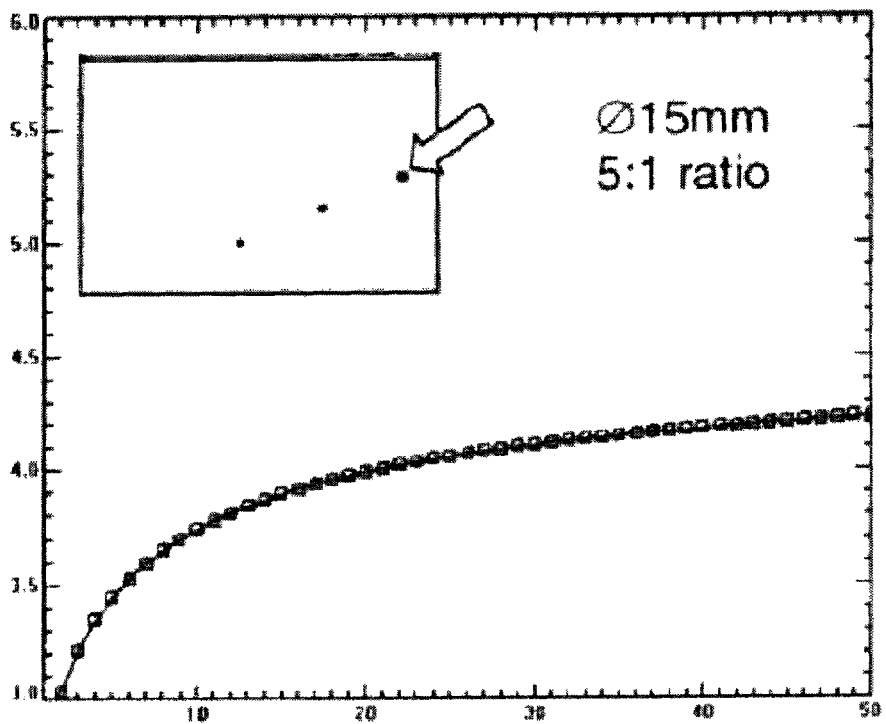

FIG. 3 illustrates an example of the time-truncation method of the present invention. A torso phantom image 30 was generated from a CT scan and various diameter "hot spheres" 31 were inserted in the phantom background. A typical scanner acquisition consists of 15 TOF bins of 0.312 ns width and 0.55 ns resolution. In accordance with the invention, a truncated time window FOV 32 was used to generate projection data only for the central 3 TOF bins. Reconstruction image 34 was obtained from the time-truncated projection data using the OS-EM algorithm with 50 iterations and 14 sunsets. As shown, the image was reconstructed exactly in the truncated time window FOV and relatively well in the areas outside of the time window FOV.

FIGS. 4A-4E show the recovery of the hot spheres as a function of iteration number, for various diameter sizes and ratios. The image inserts indicate the corresponding sphere and show the size and true ratio of the spheres. As shown, spheres that are close to the border of the time window FOV were reconstructed exactly, while one sphere, which was significantly distant from the center of the time window FOV, was smoothed.

The following references are relevant to this description and are fully incorporated herein by reference:

[1] M. Defrise, F. Noo, R. Clackdoyle and H. Kudo, "Truncated Hilbert Transform and image reconstruction from limited tomographic data," *Inv. Prob.*, Vol. 22, pp. 1037-1053, 2006.
[2] W. Wang, "Investigation of local tomography property for TOF-PET OS-EM reconstruction," *Proceedings of Fully 3D Meeting*, pp. 100-103, 2007.
[3] M. Defrise, C. Michel, M. Casey and M. Conti, "Fourier rebinning of time-of-flight PET data," *Phys. Med. Biol.*, No. 50, pp. 2749-2763, 2005.

What is claimed:

1. A method of performing TOF-PET imaging using a TOF-PET imaging apparatus, comprising acquiring projection data from a detector of said apparatus, using a truncated time window field of view (FOV) that is smaller than a maximum time window FOV obtainable by said apparatus, and reconstructing an image having a FOV represented by a time window FOV larger than said truncated time window FOV using said projection data.

2. The method of claim 1, wherein said truncated time window field of view is obtained by restricting projection data acquisition to only a central subset of TOF bins less than all available TOF bins in a TOF-PET imaging procedure.

3. The method of claim 1, further comprising reconstructing an image from said acquired projection data using an OS-EM reconstruction algorithm.

4. The method of claim 3, wherein said reconstruction is a 2D reconstruction.

5. The method of claim 3, wherein said reconstruction is a 3D reconstruction.

6. The method of claim 1, wherein said truncated time window field of view represents a region of interest of an object being imaged that is smaller than said object.

7. The method of claim 1, wherein said projection data is acquired from a $^{82}$Rb radiation distribution.

8. The method of claim 7, wherein said $^{82}$Rb radiation distribution projection data forms a cardiac study.

9. A method of reconstructing PET images from TOF-PET projection data obtained from a TOF-PET scanner by reducing a field of view of said TOF-PET scanner, comprising restricting generation of TOF-PET projection data to only TOF bins that contribute data to a specific region of interest smaller than a full field of view of said TOF-PET scanner, and reconstructing PET images corresponding to said full field of view from said projection data.

10. The method of claim 9, wherein said TOF bins comprise TOF bins in the center of said full field of view.

11. The method of claim 9, wherein said projection data is acquired from a $^{82}$Rb radiation distribution.

12. The method of claim 11, wherein said $^{82}$Rb radiation distribution projection data forms a cardiac study.

* * * * *